United States Patent [19]

Boyce et al.

[11] Patent Number: 6,063,970
[45] Date of Patent: *May 16, 2000

[54] PROCESS FOR PREPARING FLUORINATED ALIPHATIC COMPOUNDS

[75] Inventors: C. Bradford Boyce, Baton Rouge; Randolph K. Belter, Zachary; Terry Parker, Baton Rouge, all of La.

[73] Assignee: Laroche Industries, Inc., Atlanta, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 09/168,240

[22] Filed: Oct. 8, 1998

[51] Int. Cl.$^7$ .................................................. C07C 17/08
[52] U.S. Cl. ................................................... 570/168
[58] Field of Search ..................... 570/167, 168

[56] References Cited

U.S. PATENT DOCUMENTS 5,616,819  4/1997  Boyce et al. .......................... 570/167

*Primary Examiner*—Alan Siegel
*Attorney, Agent, or Firm*—Richard J. Hammond

[57] ABSTRACT

A process is disclosed for the preparation of a chlorofluoro aliphatic hydrocarbon having the formula $$CH_aF_{3-a}-CH_2-CH_cCl_{3-c-b}F_b$$

wherein a and c are 0 or the integer 1 or 2 and b is the integer 1, 2 or 3. The process comprises reacting a chlorinated fluoroolefinic hydrocarbon of the formula $$CH_aF_{3-a}-CH=CH_cCl_{2-c}$$

wherein a and c are as previously described, with anhydrous hydrogen fluoride and a is as described previously. This reaction is catalyzed with a compound that is a metal oxide or metal halide. The metallic part of such compound is arsenic, antimony, tin, boron or is selected from a metal in Group IVb, Vb, VIb, VIIb or VIIIb of the Periodic Table of the Elements. The desired chlorofluoro aliphatic hydrocarbon is then recovered.

8 Claims, No Drawings

PROCESS FOR PREPARING FLUORINATED ALIPHATIC COMPOUNDS

FIELD OF THE INVENTION

This invention relates to a process for preparing aliphatic compounds substituted with multiple fluorine atoms. In particular, this invention relates to the discovery that highly fluorinated chloro aliphatic compounds can be prepared in high yield by a process comprising a catalyzed hydrofluorination of a chlorofluoro olefin.

BACKGROUND OF THE INVENTION

The replacement of chlorofluorocarbons (CFC's) widely used in refrigerant compositions, propellants and cooling fluids as well as blowing agents, solvents and rinse agents with environmentally acceptable alternatives has produced an abundance of compounds meeting one or more of these needs. The most acceptable replacement compounds are those having little or no chlorine, since it is generally accepted that chlorinated aliphatics lead to unacceptable reactive chlorine-containing radicals when present in the upper atmosphere. These radicals are thought to react with the ozone in the stratosphere depleting it to dangerously low levels.

One of the more promising alternatives to CFC's are the aliphatic compounds where chlorine has been replaced with fluorine. These materials are known as hydrofluorocarbons (HFC's). Typical HFC's have atmospheric lifetimes and global warming potentials that are a fraction of their chlorinated analogs. However, many of their other physical properties (low flammability and toxicity, sufficient volatility, etc.) are identical or similar to the CFC'S. Accordingly, they are attractive replacements for the chlorinated molecules.

In processes for preparing HFC's, a usual starting material is the chlorinated analog of the desired fluorinated compound. Thus, U.S. Pat. No. 2,787,646 discloses that $SbF_3Cl_2$ and/or $SbF_3$ are useful for converting compounds of the formula $CMZ_2CX=CHY$, for example 3,3,3-trichloroprop-1-ene or 1,1,3-trichloroprop-1-ene to compounds of the formula $CF_3CX=CHY$, for example 3,3,3-trifluoroprop-1-ene.

U.S. Pat. No. 2,549,580 discloses the conversion of 1,1-dichloroprop-1-ene to 1,1,1-trifluoropropane by means of HF at 120° C. and 800 psi pressure.

The preparation of 1-chloro-1,1,3,3,3-pentafluoropropane and of 1,1,1,3,3,3-hexafluoropropane from 1,1,1,3,3,3-hexachloropropane in the liquid phase is described in EPO Publication No. 0 522 639 A1. While the preferred catalyst for the reaction is noted to be $SbCl_5$, other catalysts disclosed are those metal chlorides, fluorides, and chloride fluorides of Group Ma, IVa, IVb, Va, Vb and VIb of The Periodic Table of the Elements.

Compounds such as 1,1,1,3,3,3-hexafluoropropane are prepared by the coupling of two chlorine containing reactants, i.e., 1,1,1-trichloro-2,2,2-trifluoroethane and dichloro difluoromethane, in the presence of hydrogen and a first catalyst to form an olefin, i.e., 1,1,1,3,3-pentafluoro-2-chloroprop-2-ene and then hydrogenating the olefin in the presence of a second catalyst. See WO 95/05353.

Japanese Kokai JP 10-72381, published Mar. 17, 1998 discloses the disproportionation reaction of 1,1,1,3-tetrafluoro-3-chloropropane to 1,1,1,3,3-pentafluoropropane in the presence of a disproportionation catalyst that is an antimony and/or aluminum halogenated compound. The 1,1,1,3-tetrafluoro-3-chloropropane is made by the addition of hydrogen fluoride to the chlorofluoro olefin 1,1,1,-trifluoro-3-chloropropene using an antimony or boron halide catalyst at a temperature between 0° and 150° C.

SUMMARY

The process of the present invention is used to prepare a chlorofluoro aliphatic hydrocarbon of the formula

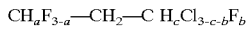

wherein a and c are 0 or the integer 1 or 2 and b is the integer 1, 2 or 3. This process utilizes a chlorinated fluoroolefinic hydrocarbon as the starting material which has the formula

wherein a and c are 0 or the integer 1 or 2. The olefinic hydrocarbon is reacted with anhydrous hydrogen fluoride. This reaction is catalyzed with a compound that is a metal oxide or metal halide. The metallic part of such compound is arsenic, antimony, tin, boron or is selected from a metal in Group IVb, Vb. VIb. VIIb or VIIIb of the Periodic Table of the Elements. The desired chlorofluoro aliphatic hydrocarbon is then recovered.

DESCRIPTION OF THE PREFERRED EMBODIMENTS

The process of the present invention is particularly useful for producing highly fluorinated aliphatic compounds that are not easily prepared in typical fluorine for chlorine substitution reactions.

Thus, for example, in the catalyzed reaction of 1,1,1,3,3-pentachloropropane with hydrogen fluoride, fluorine substitution for chlorine is accompanied by much tar and byproducts so that the pentafluoro compound is not formed in commercially acceptable yields.

Similarly, polychloro olefins such as 1,1,3,3-tetrachloroprop-1-ene with anhydrous hydrogen fluoride and a typical catalyst fail to yield the desired pentafluoropropane in acceptable yield due to extensive telomerization.

The process of the present invention overcomes these disadvantages by utilizing as the starting material, a partially fluorinated, chloro olefin of the formula

wherein a and c are 0 or the integer 1 or 2. The olefinic hydrocarbon is reacted with anhydrous hydrogen fluoride for a time and at a temperature sufficient to produce the chlorofluoro aliphatic hydrocarbon. The partially fluorinated, chloro olefin is also referred to herein as a "chlorinated fluoroolefinic hydrocarbon" and has the formula

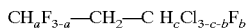

wherein a and c are 0 or the integer 1 or 2 and b is the integer 1, 2 or 3.

The reaction of the chlorinated fluoroolefinic hydrocarbon with hydrogen fluoride is catalyzed with a compound that is a metal oxide or metal halide. The metallic part of such compound is arsenic, antimony, tin, boron or is selected from a metal in Group IVb, Vb. VIb. VIIb or VIIIb of the Periodic Table of the Elements. The desired chlorofluoro aliphatic hydrocarbon is produced and then recovered by conventional means, e.g.,distillation.

In the above-disclosed first step, it is preferred that the polychloro compound is one where c is 0 or the integer 1. Most preferably, a is 0 and c is 1.

At least one mole of hydrogen fluoride are required to produce the aliphatic hydrocarbon However, an excess of hydrogen fluoride, preferably from about 2 to about 10 times the stoichiometric requirements are typically used in this reaction to facilitate the formation of the highly fluorinated chlorofluoro aliphatic hydrocarbon The catalyst is typically introduced into the reaction vessel prior to the chlorinated fluoro olefinic hydrocarbon and HF.

A variety of catalysts are useful in carrying out the reaction of the present invention. To a large extent, many of these catalysts are equivalent and the choice of which one depends on cost, availability and solubility in the reaction mass. The catalysts are metal halides or oxides, the metals being selected from the group consisting of arsenic, antimony, tin, boron, and from metals of Group IVb, Vb, VIb, VIIb, or VIb of the Periodic Table of the Elements. Preferably the metal is a chloride or fluoride, most preferably a fluoride. It is preferably antimony, arsenic, tin, bismuth or from Group IVb or VIIIb of the Periodic Table of the Elements. Preferably the catalyst is selected from the fluorides of tantalum, tin, and titanium. Most preferably, the catalyst is a mixture of tantalum (V) and titanium (IV) in a 4 to 1 molar ratio. A particularly preferred catalyst is tantalum (V) chloride. The amount of catalyst used in the reaction is sufficient to catalyze the reaction. It is at least 1 mmol and preferably about 10 to about 200 mmol, per mole of chlorinated fluoro olefinic hydrocarbon used in batch operation. At very low concentrations, the reaction may be unacceptably slow and at very high concentrations may be wasteful due to the fact that the solubility limit may have been reached at even lower catalyst to chlorofluoro olefinic hydrocarbon ratios. Consequently, the most preferred amount of catalyst is from about 10 to about 50 mmol, per mole of chlorofluoro olefinic hydrocarbon.

The reaction can be carried out as a batch or continuous process. In the batch mode, the chlorinated fluoro olefinic hydrocarbon starting material may be added to the reaction vessel first. Order of addition is not critical. Hydrogen fluoride is introduced and the reaction vessel heated, with agitation, to a temperature and over a period of time sufficient to produce the desired chlorofluoro aliphatic hydrocarbon, i.e., a temperature of from about 70° C. to about 120° C., preferably about 80° C. to about 100° C., for from 15 minutes to 24 hours According reaction is run in the liquid phase for convenience although the reaction may be run in the vapor phase over an appropriate surface such as aluminum fluoride.

At the conclusion of the reaction time, the reaction vessel is cooled to 50° C. and the product aliphatic hydrocarbon and excess HF is then distilled, permitting ready isolation of the desired aliphatic hydrocarbon product.

The continuous mode requires continuous mixing at a flow rate and temperature sufficient to assure the contact times at the required temperature noted above. Continuous removal of the fluorochloro aliphatic hydrocarbon product is, of course required A particularly preferred embodiment of the present invention is the process to produce a chlorofluoro aliphatic compound of the formula $$CF_3-CH_2-CHFCl$$

i.e., the compounds where a and c are 0 and b is the integer 1. Such process comprises reacting a chlorinated fluoroolefinic hydrocarbon of the formula $$CF_3-CH=CHCl$$

with anhydrous hydrogen fluoride. This reaction is catalyzed with a compound that is a metal oxide or metal halide. The metallic part of such compound is arsenic, antimony, tin, boron or is selected from a metal in Group IVb, Vb. VIb. VIIb or VIIIb of the Periodic Table of the Elements. The desired chlorofluoro aliphatic hydrocarbon is then recovered.

Other particularly preferred compounds prepared in accordance with the process of the present invention are those of the formula $$CHF_2-CH_2-CHFCl \text{ and } CF_3-CH_2-CFCl_2$$

EXAMPLE 1

The results of the catalyzed reaction of 1,1,1-trifluoro-1-chloropropene with anhydrous hydrogen fluoride to produce 1,1,1,3-tetrafluoro-3-chloropropane is shown in the following table.

TABLE $CF_3 - CH = CHCl \rightarrow CF_3 - CH_2 - CHFCl$
(Starting Material) (ClF4-ane)

| Catalyst | ClF4-ane | Starting Material | HFC 245fa |
|---|---|---|---|
| TaCl$_5$ | 62 | 36 | <2 |
| 4TaCl$_5$\TiCl$_4$ | 21 | 65 | 10 |
| TiCl$_4$\MeSO$_2$Cl | 58 | 13 | 16 |
| TiCl$_4$\sulfolane | 11 | 86 | <1 |
| TiCl$_4$ | 19 | 19 | 57 |
| SbCl$_5$ | 19 | 0 | 73 |
| 4SbCl$_5$\TiCl$_4$ | 20 | 0 | 72 |
| 4Sb\Ti\Ph—CF$_3$ | 66 | 0 | 33 |
| *VCl$_3$* | 8 | 90 | 0 |
| *4SbCl$_5$\SnCl$_4$* | 8 | 7 | 77 |
| *4SbCl$_5$\SbCl$_3$* | 3 | 3 | 92 |
| *SnCl$_4$\TiCl$_4$* | 1 | 99 | 0 |
| *SnCl$_4$* | 0 | 100 | 0 |
| *4TiCl$_4$\TaCl$_5$* | 0 | 100 | 0 |
| *BF$_3$* | 0 | 100 | 0 |

Note: Catalysts shown in italics are Examples submitted for comparison purposes

We claim:

1. A process for preparing a chlorofluoro aliphatic hydrocarbon selected from the group consisting of 1-chloro-1,3,3,3-tetrafluoropropane, 1-chloro-1,3,3-trifluoropropane and 1,1-dichloro-1,3,3,3-tetrafluoropropane comprising reacting a chlorinated fluoroolefinic hydrocarbon of the formula $$CH_aF_{3-a}-CH=CH_cCl_{2-c}$$

where a is 0 or the integer 1 or 2 and c is 0 the integer 1, with anhydrous hydrogen fluoride and a catalytically effective amount of a catalyst selected from the group consisting of the halides of tantalum, vanadium, and mixtures thereof for a time and at a temperature sufficient to form said chlorofluoro aliphatic hydrocarbon.

2. The process according to claim 1 wherein a, b and c are the integer 1.

3. The process according to claim 1 wherein a and b are the integer 1 and c is the integer 0.

4. The process according to claim 1 wherein a and c are 0 and b is the integer 1.

5. The process according to claim 1 wherein a is 0 and b and c are the integer 1.

6. The process according to claim 1 wherein carried out in the liquid phase.

7. The process according to claim 1 wherein said temperature is from about 25° C. to about 150° C.

8. The process according to claim 1 wherein said temperature is from about 50° C. to about 75° C.

* * * * *